United States Patent
Schneider

(10) Patent No.: US 6,369,271 B1
(45) Date of Patent: Apr. 9, 2002

(54) PROCESS FOR PREPARING DERIVATIVES OF BIPHENYL-2-CARBOXYLIC ACID

(75) Inventor: Heinrich Schneider, deceased, late of Ingelheim (DE), by Margarete Schneider, legal representative

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/510,556

(22) Filed: Feb. 22, 2000

Related U.S. Application Data
(60) Provisional application No. 60/128,309, filed on Apr. 8, 1999.

(30) Foreign Application Priority Data

Feb. 26, 1999 (DE) .......................... 199 08 504

(51) Int. Cl.[7] ...................... C07C 63/33; C07C 63/333; C07D 263/52
(52) U.S. Cl. ...................... 562/492; 562/492; 562/469; 548/216
(58) Field of Search ................ 562/492, 469; 548/216

(56) References Cited

FOREIGN PATENT DOCUMENTS

| EP | 0 059 983 | 9/1982 |
| JP | 52 023 058 | 2/1977 |

OTHER PUBLICATIONS

Meyers et al, J. Am. Chem. Soc. vol. 97, pp. 7383–7385, 1975.*

Carini et al, J. Med. Chem. vol. 34, No. 8, pp. 2525–2547, 1991.*

Eaddy et al, Org. Perp. Proced. Int., 27(3), 367–72, 1995).*

* cited by examiner

Primary Examiner—Paul J. Killos
Assistant Examiner—Farhad Forohar
(74) Attorney, Agent, or Firm—R. P. Raymond; T. X. Witkowski

(57) ABSTRACT

The invention relates to a process for large-scale industrial production of biphenyl-2-carboxylic acid derivatives (I)

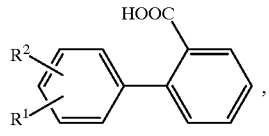

wherein $R^1$ and $R^2$ may have the meanings given in the specification and claims.

12 Claims, No Drawings

PROCESS FOR PREPARING DERIVATIVES OF BIPHENYL-2-CARBOXYLIC ACID

RELATED APPLICATIONS

Benefit of U.S. Provisional Application Serial No. 60/128,309, filed on Apr. 8, 1999, is hereby claimed.

FIELD OF THE INVENTION

The invention relates to a process which can be used on an industrial scale for preparing biphenyl-2-carboxylic acid derivatives (I)

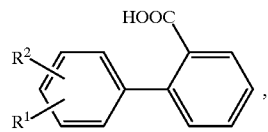

wherein $R^1$ and $R^2$ may have the meanings given in the specification and claims.

BACKGROUND OF THE INVENTION

Biphenyl-2-carboxylic acids of formula (I) are very important as intermediate products in the production of pharmaceutically valuable active substances, particularly in the production of pharmaceutical substances which may be used as angiotensin-II-antagonists.

Processes for preparing biphenyl-2-carboxylic acid and the derivatives (I) thereof are known from the prior art. One method essential to the background of the invention is the coupling of aromatic Grignard compounds (II) with optionally substituted (2-methoxy-phenyl)-2-oxazolines (III) according to Diagram 1, as described by Meyers et al. (e.g. Tetrahedron (1985) Vol. 41, 837–860), in which the corresponding (2-oxazolinyl)-2-biphenyl derivatives (IV) are obtained to begin with.

carboxylic acid, starting from biphenyl-oxazoline unsubstituted at the oxazoline group (i.e. $R^1$ and $R^2$=hydrogen; $R^{Ox}$=oxazolin-2-yl).

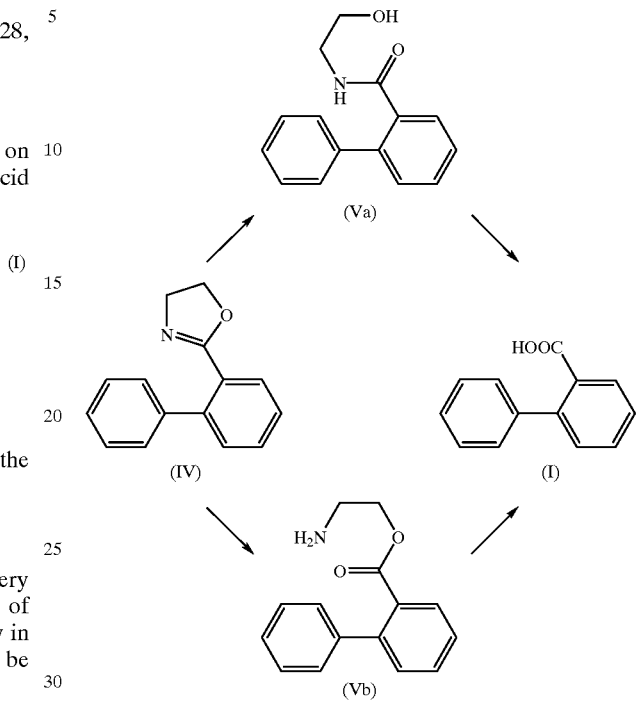

Diagram 2:

The saponification of the oxazoline under reaction conditions known in the art leads in the first step to the formation of the aminoester (Vb) (Meyers et al. *J. Org. Chem.* (1974) Vol. 39, 2787–2793). The aminoester (Vb) can then be saponified to the carboxylic acid (I) in a second reaction step, e.g. by boiling for several hours in 10–25% sodium hydroxide solution.

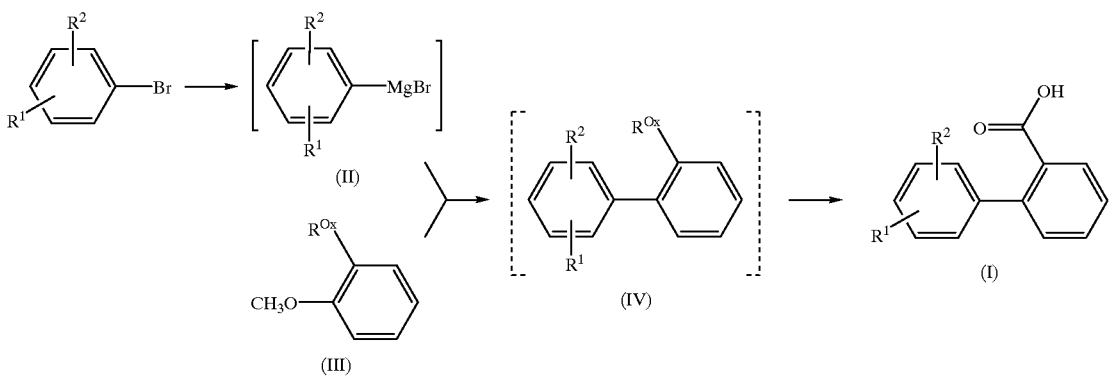

Diagram 1:

The group $R^{Ox}$ denotes an optionally substituted oxazolin-2-yl group. The definition of the groups $R^1$ and $R^2$ can be found in the later part of the specification and in the claims. Conversion into the corresponding carboxylic acids of formula (I) is effected by saponification of the oxazolines (IV). This saponification of (IV) can be carried out by two different reaction methods, from a formal point of view. In Diagram 2 these reaction methods are illustrated by way of example with reference to the preparation of biphenyl-2-

For a large-scale manufacturing process, however, it is desirable to carry out the saponification process as a one-pot process.

The acid saponification by a one-pot process (e.g. according to EP59983) carried out using the methods known from the prior art, however, led to unsatisfactory results when done on a large scale.

It was observed that because of the low solubility in the solvents which are used according to the prior art (e.g. aqueous hydrochloric acid according to EP 59983) aminoester (Vb) is partially precipitated after being formed. A precipitate of (Vb) is formed on the stirring mechanism and on the walls of the reaction vessel. This causes aminoester (Vb) to be removed successively from the reaction solution and, because of the poor solubility, it is then virtually no longer available for farther reaction to form the desired end compound (I). A further reduction in yield occurs as a result of the inclusion of product (I) in the crystallised aminoester (Vb) which is clumping normally.

The abovementioned disadvantages lead to an increased cost in the large-scale production of (I), since within the scope of the working up and processing of the end product, on the one hand, the aminoester (Vb) has to be separated off and, on the other hand, a separate synthesis step has to take place for reacting the precipitated aminoester (Vb) to form the end product.

The aim and objective of the present invention is therefore to provide a process for preparing derivatives/homologues of biphenyl-2-carboxylic acid on a large scale which overcomes the disadvantages of the processes known from the prior art.

DETAILED DESCRIPTION OF THE INVENTION

Surprisingly, it has been found that the disadvantages encountered in the methods of preparing biphenyl-2-carboxylic acid derivatives known from the prior art can be avoided if the saponification of the oxazoline (IV) is carried out with hydrochloric acid at elevated temperature under pressure, in the presence of an inert organic solvent which is immiscible with water.

The present invention is consequently directed to a large-scale process for preparing biphenyl-2-carboxylic acid derivatives of general formula (I)

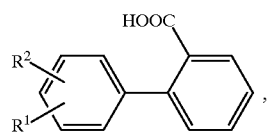

(I)

wherein
- $R^1$ and $R^2$ which may be identical or different denote hydrogen, $C_1$–$C_6$-alkyl, which may optionally be substituted by halogen, $C_1$–$C_6$-alkoxy, $C_1$–$C_6$-acyl, $C_1$–$C_6$-alkoxycarbonyl, COOH, phenyl, benzyl, halogen, hydroxy, nitro or amino, or wherein
- $R^1$ and $R^2$ together with adjacent carbon atoms of the phenyl ring form a saturated or unsaturated 5- or 6-membered carbocyclic group which may optionally be substituted by $C_1$–$C_4$-alkyl, halogen, COOH, phenyl or hydroxy;

characterised in that a (2-oxazolinyl)-2-biphenyl derivative of general formula (IV)

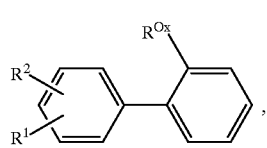

(IV)

wherein
$R^1$ and $R^2$ are as hereinbefore defined and $R^{Ox}$ denotes an oxazolin-2-yl group, which may optionally be mono-, di-, tri- or tetra-substituted by one or more of the groups $C_1$–$C_6$-alkyl, which may optionally be substituted by halogen, hydroxy or $C_1$–$C_4$-alkoxy, $C_1$–$C_6$-alkoxy, phenyl, which may optionally be substituted by $C_1$–$C_4$-alkyl, $C_1$–$C_4$-alkoxy, hydroxy, nitro or amino, benzyl, pyridyl or $C_1$–$C_6$-alkoxycarbonyl, is saponified with hydrochloric acid at elevated temperature under pressure, in the presence of an inert organic solvent which is immiscible with water.

A preferred process according to the invention is a process for preparing biphenyl-2-carboxylic acid derivatives of general formula (I) wherein
- $R^1$ and $R^2$, which may be identical or different, denote hydrogen, $C_1$–$C_4$-alkyl, which may optionally be substituted by fluorine, chlorine or bromine, $C_1$–$C_4$-alkoxy, $C_1$–$C_4$-acyl, $C_1$–$C_4$-alkoxycarbonyl, COOH, phenyl, benzyl, fluorine, chlorine, bromine, hydroxy, nitro or amino, or wherein
- $R^1$ and $R^2$ together with adjacent carbon atoms of the phenyl ring form an unsaturated 6-membered carbocyclic group which may optionally be substituted by $C_1$–$C_4$-alkyl, fluorine, chlorine, bromine, COOH, phenyl or hydroxy;

characterised in that a (2-oxazolinyl)-2-biphenyl derivative of general formula (IV),
wherein
$R^1$ and $R^2$ are as hereinbefore defined and
$R^{Ox}$ denotes an oxazolin-2-yl group, which may optionally be mono- or disubstituted by one or more of the groups $C_1$–$C_4$-alkyl, which may optionally be substituted by fluorine, chlorine, bromine, hydroxy or $C_1$–$C_4$-alkoxy, $C_1$–$C_4$-alkoxy, phenyl, which may optionally be substituted by $C_1$–$C_4$-alkyl, $C_1$–$C_4$-alkoxy, hydroxy, nitro or amino, benzyl or $C_1$–$C_4$-alkoxycarbonyl, is saponified with hydrochloric acid at elevated temperature under pressure, in the presence of an inert organic solvent which is immiscible with water.

Particularly preferred is a process for preparing biphenyl-2-carboxylic acid derivatives of general formula (I), wherein
- $R^1$ and $R^2$ which may be identical or different, denote hydrogen, methyl, ethyl, n-propyl, iso-propyl, n-butyl, tert-butyl, $CF_3$, methoxy, ethoxy, COOH, phenyl, benzyl, fluorine, chlorine, bromine, hydroxy, nitro or amino, or wherein
- $R^1$ and $R^2$ together with adjacent carbon atoms of the phenyl ring form an anellated phenyl ring which may optionally be substituted by methyl, ethyl, n-propyl, isopropyl, tert.-butyl, fluorine, chlorine, bromine, COOH, phenyl or hydroxy, characterised in that a (2-oxazolinyl)-2-biphenyl derivative of general formula (IV)
wherein
$R^1$ and $R^2$ are as hereinbefore defined and
$R^{Ox}$ denotes an oxazolin-2-yl group, which may optionally be mono- or disubstituted by one or more of the groups methyl, ethyl, n-propyl, iso-propyl, n-butyl, tert.-butyl, methoxymethyl, hydroxymethyl, methoxy or ethoxy, or phenyl, which may optionally be substituted by methyl, ethyl, n-propyl, iso-propyl, n-butyl, tert.-butyl, methoxy, ethoxy or hydroxy, or benzyl, methoxycarbonyl or ethoxycarbonyl, is saponified with hydrochloric acid at elevated temperature under pressure, in the presence of an inert organic solvent which is immiscible with water.

Also of importance according to the invention is a process for preparing biphenyl-2-carboxylic acid derivatives of general formula (I), wherein $R^1$ and $R^2$ which may be identical or different, denote hydrogen, methyl, $CF_3$, COOH, phenyl, fluorine or hydroxy, or wherein $R^1$ and $R^2$ together with adjacent carbon atoms of the phenyl ring form an anellated phenyl ring, characterised in that a (2-oxazolinyl)-2-biphenyl derivative of general formula (IV),
wherein $R^1$ and $R^2$ are as hereinbefore defined and $R^{Ox}$ denotes an oxazolin-2-yl group, which may optionally be mono- or disubstituted by one or more of the groups methyl, ethyl, methoxy, ethoxy, phenyl or benzyl, is saponified with hydrochloric acid at elevated temperature under pressure, in the presence of an inert organic solvent which is immiscible with water.

Of particular importance is a process for preparing biphenyl-2-carboxylic acid derivatives of general formula (I), wherein $R^1$ and $R^2$ which may be identical or different, denote hydrogen, methyl or $CF_3$, characterised in that a (2-oxazolinyl)-2-biphenyl derivative of general formula (IV),
wherein $R^1$ and $R^2$ are as hereinbefore defined and $R^{Ox}$ denotes an oxazolin-2-yl group optionally mono- or disubstituted by methyl, is saponified with hydrochloric acid at elevated temperature under pressure, in the presence of an inert organic solvent which is immiscible with water.

It is particularly preferable according to the invention to operate as follows. 0.08–0.8, preferably 0.15–0.5, most preferably about 0.2 l water and 3.0–6.0 mol, preferably 3.5–5.0 mol, most preferably about 4.0 mol hydrochloric acid per mol of oxazolin-2-yl-biphenyl (IV) are placed in a reaction vessel of suitable size. Preferably, the abovementioned hydrochloric acid is added in the form of aqueous solutions, most preferably in the form of 36.5% aqueous solution, so that a hydrochloric acid concentration of 20–30%, most preferably about 24% is produced.

After rendering inert with protective gas, preferably nitrogen, the reaction vessel is evacuated (to about 50 mbar) and 0.05–0.2, preferably 0.08–0.15, most preferably about 0.1 litre of an inert organic solvent is added per mol of starting compound (IV) used. According to the invention, aliphatic or aromatic hydrocarbons and aromatic chlorohydrocarbons with 6–10 carbon atoms may be used as inert organic solvents. Aliphatic or aromatic hydrocarbons with 7–8 carbon atoms are preferred. The solvents which may be used according to the invention are preferably toluene, xylene, chlorobenzene and methylcyclohexane. Methylcyclohexane is particularly preferred.

After the addition of the inert organic solvent the reaction solution is heated to a temperature in the range from 120–160° C., preferably 130–150° C., most preferably 140–145° C. At constant temperature the mixture is stirred for a further 3–10 h, preferably 4–8 hours. The apparatus is sealed (in practice by closing the vapour seal valve), so that the heating of the reaction solution mentioned above produces an internal pressure of 3–6 baro (=bars overpressure), preferably 4–5 baro within the apparatus. The temperature can be varied depending on the boiling point of the solvent used, so that the abovementioned internal pressure is built up. This results in the additional advantage according to the invention that conventional apparatus such as DIN enamel apparatus (to pressure level 6 baro) can be used.

The reaction vessel is then cooled to a temperature at which the apparatus is at maximum atmospheric pressure (20–50° C.). Any underpressure is optionally equalised with inert gas.

For working up, the reaction mixture is combined with a suitable solvent or mixture of solvents which enables the aqueous hydrochloric acid phase to be separated off without loss of product. It is preferable to use toluene, xylene or methylcyclohexane in admixture with tetrahydrofuran. A mixture of toluene and tetrahydrofuran in a ratio of about 1:1 is particularly preferred. Between 0.1 and 1 litre of the above mentioned organic solvent or mixture of solvents are used per mol of starting compound (IV) used. Preferably, 0.2–0.5 l of the above mentioned organic solvent or mixture of solvents are used per mol of oxazoline (IV) put in. Most preferably, about 0.3 to 0.35 l of the organic solvent or mixture of solvents are used per mol of oxazoline (IV) put in.

The aqueous lower phase is then separated off and the remaining upper phase is extracted several times, preferably 2–3 times, most preferably twice with water. According to the invention, the amount of washing water used for each extraction process is within a range of from 0.05–0.5 l water per mol of oxazoline (IV) used. Preferably, in each extraction step, 0.1–0.2 litres of water are used per mol of starting compound (IV) put in.

The washed organic upper phase is then made alkaline. This may be done according to the invention with aqueous solutions of alkali metal or alkaline earth metal hydroxides. Preferably, aqueous solutions of lithium, sodium or potassium hydroxide are used. According to the invention, aqueous sodium hydroxide solution is particularly preferred as the base. 0.7–1 mol of base, preferably 0.8–0.9 mol of base are used per mol of starting compound (IV).

After the phase separation has taken place the lower phase is decanted into another reaction vessel. The upper phase remaining is then subjected to the above mentioned alkalisation. According to the invention, however, only about 10% w/w of the quantity of base used in the first alkalisation step are added. Once the lower phase has been separated off, the combined aqueous extracts are freed from any entrained solvent by distillation. About 0.05–0.5 l water, preferably between 0.07 and 0.2 l, most preferably about 0.1 litres of water are distilled off per mol of starting compound (IV) used. After cooling to a temperature below 40° C., preferably to a temperature in the range from 20–30° C., most preferably to 25° C., 0.1–0.5 l, preferably about 0.2 l of water are added per mol of starting compound put in and the mixture is then made acidic with 1–5 mol, preferably, 2–4 mol, most preferably about 3.5 mol hydrochloric acid.

The product precipitated is centrifuged, washed with water and dried.

The Examples which follow serve to illustrate some methods of synthesising derivatives of biphenyl-2-carboxylic acid of general formula (I) carried out by way of example, according to the invention. They should be understood as being purely possible procedures described by way of example, without restricting the invention to their contents.

EXAMPLE 1

265 kg of 4'-methyl-2-(4,4-dimethyloxazolin-2-yl) biphenyl, 205 l of water and 400 kg of 36.5% hydrochloric acid are placed in a 1200 l enamel stirring apparatus. After it has been rendered inert with nitrogen it is evacuated to about 50 mbar and then 102.5 l of methylcyclohexane are added. After the vapour seal valve has been closed the apparatus is heated to about 140° C. within about 1 h and then stirred for a further 4 to 8 h at 140–145 ° C. An internal pressure of 4–5 baro is built up. Then the apparatus is cooled to 20–30° C., adjusted to atmospheric pressure with nitrogen and 175 l of toluene and 150 l of TBF are added. The aqueous lower phase is separated off and the organic upper phase remaining is extracted with 205 l and then with 103 l of water. A further 512 l of water and 80 kg of 45% sodium hydroxide solution are added to the upper phase and, after settling, the lower phase is drained off into another 1200 l enamel stirring apparatus. This operation is repeated with 103 litres of water and 8.9 kg of 45% sodium hydroxide solution. To begin with, about 103 l are distilled off from the combined aqueous extracts and after cooling to 25° C., 205 litres of water and then 97 kg of 36.5% hydrochloric acid are added. The product is centrifuged, washed with water and dried.

Yield: 190 kg of 4'-methylbiphenyl-2-carboxylic acid (90%)

EXAMPLE 2

251 kg of 2-(4,4-dimethyloxazolin-2-yl)biphenyl, 205 l of water and 400 kg of 36.5% hydrochloric acid are placed in a 1200 l enamel stirring apparatus. After it has been rendered inert with nitrogen it is evacuated to about 50 mbar and then 102.5 l of methylcyclohexane are added. After the vapour seal valve has been closed the apparatus is heated to about 140° C. within about 1 h and then stirred for a further 4 to 8 h at 140–145 ° C. An internal pressure of 4–5 baro is built up. Then the apparatus is cooled to 20–30° C., adjusted to atmospheric pressure with nitrogen and 175 l of toluene and 150 l of THF are added. The aqueous lower phase is separated off and the organic upper phase remaining is extracted with 205 l and then with 103 l of water. A further 512 l of water and 80 kg of 45% sodium hydroxide solution are added to the upper phase and, after settling, the lower phase is drained off into another 1200 l enamel stirring apparatus. This operation is repeated with 103 litres of water and 8.9 kg of 45% sodium hydroxide solution. To begin with, about 103 l are distilled off from the combined aqueous extracts and after cooling to 25° C., 205 litres of water and then 97 kg of 36.5% hydrochloric acid are added. The product is centrifuged, washed with water and dried.

Yield: 180 kg of biphenyl-2-carboxylic acid (91%)

COMPARISON EXAMPLE 265 kg of 4'-methyl-2-(4,4-dimethyloxazolin-2-yl) biphenyl, 205 l of water and 400 kg of 36.5% hydrochloric acid are placed in a 1200 l enamel stirring apparatus. After it has been rendered inert with nitrogen, evacuated to about 50 mbar and the vapour seal valve has been closed, the contents of the apparatus are heated to about 140° C. within about 1 h and then stirred for a further 4 to 8 h at 140–145° C., during which time an internal pressure of 4–5 baro is built up. Then the apparatus is cooled to 20–30° C., adjusted to atmospheric pressure with nitrogen and 175 l of toluene and 150 l of THF are added. The aqueous lower phase is added to the waste water and the organic upper phase remaining is extracted with 205 l and then with 103 l of water. A further 512 l of water and 80 kg of 45% sodium hydroxide solution are added to the upper phase and, after settling, the lower phase is drained off into another 1200 l enamel stirring apparatus. This operation is repeated with 103 litres of water and 8.9 kg of 45% sodium hydroxide solution. To begin with, about 103 l are distilled off from the combined aqueous extracts and after cooling to 25° C., 205 litres of water and then 97 kg of 36.5% hydrochloric acid are added. The product is centrifuged, washed with water and dried.

Yield: 100 kg of 4'-methylbiphenyl-2-carboxylic acid (47%)

What is claimed is:

1. A process for preparing a compound of the formula (I)

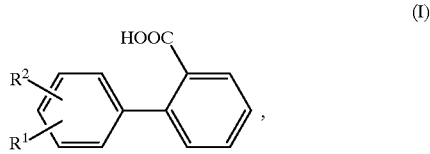

wherein:

$R^1$ and $R^2$, which are identical or different, are each hydrogen; $C_1$–$C_6$-alkyl optionally substituted by halogen; $C_1$–$C_6$-alkoxy; $C_1$–$C_6$-acyl; $C_1$–$C_6$-alkoxycarbonyl; COOH; phenyl; benzyl; halogen; hydroxy; nitro; or amino, or $R^1$ and $R^2$ together with adjacent carbon atoms of the phenyl ring form a saturated or unsaturated 5- or 6-membered carbocyclic group optionally substituted by $C_1$–$C_4$-alkyl, halogen, COOH, phenyl, or hydroxy groups, the process comprising: saponifying with hydrochloric acid at elevated temperature under pressure, in the presence of an organic solvent selected from an aliphatic or aromatic hydrocarbon or an aromatic chlorohydrocarbon with 6–10 carbon atoms, a compound of the formula (IV)

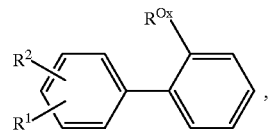

wherein:

$R^1$ and $R^2$ are as hereinbefore defined in this claim, and $R^{Ox}$ is an oxazolin-2-yl group optionally mono-, di-, tri- or tetra-substituted by groups selected from $C_1$–$C_6$-alkyl group optionally substituted by halogen, hydroxy or $C_1$–$C_4$-alkoxy; $C_1$–$C_6$-alkoxy; phenyl optionally substituted by $C_1$–$C_4$-alkyl, $C_1$–$C_4$-alkoxy, hydroxy, nitro, or amino; benzyl; pyridyl; or $C_1$–$C_6$-alkoxycarbonyl.

2. The process according to claim 1, wherein:

$R^1$ and $R^2$, which are identical or different, are each hydrogen; $C_1$–$C_4$-alkyl optionally substituted by fluorine, chlorine, or bromine; $C_1$–$C_4$-alkoxy; $C_1$–$C_4$-acyl; $C_1$–$C_4$-alkoxycarbonyl; COOH; phenyl; benzyl; fluorine; chlorine; bromine; hydroxy; nitro; or amino, or $R^1$ and $R^2$ together with adjacent carbon atoms of the phenyl ring form an unsaturated 6-membered carbocyclic group optionally substituted by $C_1$–$C_4$-alkyl, fluorine, chlorine, bromine, COOH, phenyl, or hydroxy groups; and $R^{Ox}$ is an oxazolin-2-yl group optionally mono- or disubstituted by groups selected from $C_1$–$C_4$-alkyl optionally substituted by fluorine, chlorine, bromine, hydroxy, or $C_1$–$C_4$-alkoxy; $C_1$–$C_4$-alkoxy; phenyl optionally substituted by $C_1$–$C_4$-alkyl, $C_1$–$C_4$-alkoxy, hydroxy, nitro, or amino; benzyl; or $C_1$–$C_4$-alkoxycarbonyl.

3. The process according to claim 1, wherein:

$R^1$ and $R^2$, which are identical or different, are hydrogen, methyl, ethyl, n-propyl, isopropyl, n-butyl, tert-butyl, $CF_3$, methoxy, ethoxy, COOH, phenyl, benzyl, fluorine, chlorine, bromine, hydroxy, nitro, or amino, or $R^1$ and $R^2$ together with adjacent carbon atoms of the phenyl ring form an anellated phenyl ring optionally substituted by methyl, ethyl, n-propyl, isopropyl, tert-butyl, fluorine, chlorine, bromine, COOH, phenyl, or hydroxy; and $R^{Ox}$ is an oxazolin-2-yl group optionally mono- or disubstituted by groups selected from methyl; ethyl; n-propyl; isopropyl; n-butyl; tert-butyl; methoxymethyl; hydroxymethyl; methoxy; ethoxy; phenyl optionally substituted by methyl, ethyl, n-propyl, isopropyl, n-butyl, tert-butyl, methoxy, ethoxy or hydroxy; benzyl; methoxycarbonyl; or ethoxycarbonyl.

4. The process according to claim 1, wherein:

$R^1$ and $R^2$, which are identical or different, are each hydrogen, methyl, $CF_3$, COOH, phenyl, fluorine, or hydroxy, or $R^1$ and $R^2$ together with adjacent carbon atoms of the phenyl ring form an anellated phenyl ring; and $R^{Ox}$ is an oxazolin-2-yl group optionally mono- or disubstituted by groups selected from methyl, ethyl, methoxy, ethoxy, phenyl, or benzyl.

5. The process according to claim 1, wherein:

$R^1$ and $R^2$, which are identical or different, are each hydrogen, methyl, or $CF_3$; and $R^{Ox}$ is an oxazolin-2-yl group optionally mono- or disubstituted by methyl.

6. The process according to claim 1, wherein the saponification is carried out at a pressure of 4 bar to 5 bar.

7. The process according to claim 1, wherein 3.0 moles to 6.0 moles of hydrochloric acid are used for the saponification per mole of starting compound of the formula (IV).

8. The process according to claim 1, wherein 3.5 moles to 5.0 moles of hydrochloric acid are used for the saponification per mole of starting compound of the formula (IV).

9. The process according to claim 1, wherein an aliphatic or aromatic hydrocarbon with 7–8 carbon atoms or chlorobenzene is used as the organic solvent.

10. The process according claim 1, wherein a mixture of toluene, xylene, chlorobenzene, and methylcyclohexane is used as the organic solvent.

11. The process according to claim 1, wherein methylcyclohexane is used as the organic solvent.

12. The process in accordance with claim 1, wherein the compound of formula I made is 4'-methylbiphenyl-2-carboxylic acid.

* * * * *